(12) United States Patent
Link et al.

(10) Patent No.: US 7,753,522 B2
(45) Date of Patent: Jul. 13, 2010

(54) FOCUSING DEVICE FOR OPHTHALMOLOGICAL APPLIANCES, ESPECIALLY FOR FUNDUS CAMERAS, AND METHOD FOR THE USE THEREOF

(75) Inventors: Guenter Link, Lehesten (DE); Detlef Biernat, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 17 days.

(21) Appl. No.: 11/792,432

(22) PCT Filed: Jan. 18, 2006

(86) PCT No.: PCT/EP2006/000379

§ 371 (c)(1),
(2), (4) Date: Jun. 6, 2007

(87) PCT Pub. No.: WO2006/077078

PCT Pub. Date: Jul. 27, 2006

(65) Prior Publication Data

US 2008/0030681 A1     Feb. 7, 2008

(30) Foreign Application Priority Data

Jan. 21, 2005 (DE) ................. 10 2005 003 440

(51) Int. Cl.
*A61B 3/10* (2006.01)
*A61B 3/14* (2006.01)
(52) U.S. Cl. .................. 351/205; 351/210; 351/221
(58) Field of Classification Search ......... 351/205–206, 351/210–211, 221
See application file for complete search history.

(56) References Cited

U.S. PATENT DOCUMENTS

| 4,196,979 A | 4/1980 | Kohayakawa et al. |
| 4,436,388 A | 3/1984 | Takahashi et al. |
| 4,452,517 A | 6/1984 | Kohayakawa |
| 4,544,248 A | 10/1985 | Nunokawa |

(Continued)

FOREIGN PATENT DOCUMENTS

DE    31 16 380    2/1982

(Continued)

*Primary Examiner*—Scott J Sugarman
*Assistant Examiner*—Dawayne A Pinkney
(74) *Attorney, Agent, or Firm*—Frommer Lawrence & Haug LLP

(57) ABSTRACT

The invention is directed to a method and a device for opthalmological equipment for examining the fundus of the eye by means of an optical system and electronic sensors for image recording. The focusing device, according to the invention, for opthalmological equipment based on the nonmydriatic principle comprises a projection unit which projects at least one focusing mark in the infrared spectral region on a surface in the eye and a focusing unit, both of which are displaceable along the optical axis. The displacement carried out by electronically controllable adjusting elements is carried out simultaneously or individually based on the corresponding presets of a control unit that is provided. The necessary synchronization between the projection unit and the focusing unit can be ensured in a simple manner by means of the inventive solution. Accordingly, not only can the sequence of displacement paths be optimally adapted over the entire focusing range, but the tolerances of the optics assemblies can also be compensated individually in a simple manner from one device to another.

13 Claims, 2 Drawing Sheets

U.S. PATENT DOCUMENTS 5,371,557 A 12/1994 Nanjho et al.
5,767,940 A * 6/1998 Hayashi et al. ............. 351/205
5,777,340 A 7/1998 Ueno
5,787,890 A * 8/1998 Reiter et al. ................ 600/476

FOREIGN PATENT DOCUMENTS

JP 11-56783 3/1999

* cited by examiner

FOCUSING DEVICE FOR OPHTHALMOLOGICAL APPLIANCES, ESPECIALLY FOR FUNDUS CAMERAS, AND METHOD FOR THE USE THEREOF

CROSS-REFERENCE TO RELATED APPLICATIONS

This application claims priority of International Application No. PCT/EP2006/000379, filed Jan. 18, 2006 and German Application No. 10 2005 003 440.3, filed Jan. 21, 2005, the complete disclosures of which are hereby incorporated by reference.

BACKGROUND OF THE INVENTION a) Field of the Invention

The invention is directed to a method and a device for opthalmological equipment, preferably fundus cameras, for examining the fundus of the eye by means of an optical system and electronic sensors for image recording.

b) Description of the Related Art

In order to examine the fundus of the eye with a fundus camera, it is necessary either to dilate the patient's pupil medicinally or to use fundus cameras operating by the nonmydriatic principle in which the fundus is illuminated by (invisible) infrared light so that the pupil is dilated in a darkened room without medication. When the pupil is sufficiently dilated, the eye is illuminated briefly (e.g., by means of a strobe) by white (visible) light and an image of the fundus is recorded.

To compensate for defective vision in patients, it is necessary to be able to focus fundus cameras in a corresponding manner. By displacing internal optics assemblies, a sharp, high-contrast image of the patient's fundus is formed on the image recorder or in the eye of the observer.

On principle in nonmydriatic fundus cameras, infrared light is used for observation and the resulting image is recorded with white light of a shorter wavelength. Owing to optical factors, there are different focal planes for these different wavelengths so that whereas the imaging is focused during observation with infrared light, the resulting image with white light would be recorded out of focus. For this reason, focusing means are used in nonmydriatic fundus cameras. During observation, a test mark is projected on the fundus by this device, for example, with low-intensity white light, and is evaluated accordingly. The evaluation is preferably carried out using a coincidence method in which two half-marks are made to coincide so as to determine the optimum focal plane for white light.

This embodiment form is disadvantageous in that the visible light of the test mark can cause a pupillary reaction in the patient in spite of its low intensity and therefore can make it substantially more difficult to work with the opthalmological equipment which requires a minimum pupil diameter.

In another embodiment form, the test mark is generated by means of infrared light. While this has the advantage that it does not lead to pupillary reactions in the patient, whose pupil remains dilated, it has the drawback that the infrared light is reflected in a deeper tissue layer than the white light used for image recording due to the spectral characteristics of the fundus. Therefore, a suitable optical element is required to correct the focal plane when changing from observation and focusing of the test mark to recording of the resulting image.

Whereas the test mark of focusing means is reflected at the edge of the pupil over the illumination beam path in the patient's eye, observation is carried out over the observation beam path through the center of the patient's pupil. Owing to the fact that different optical elements are used in the illumination beam path and observation beam path, there is a complicated nonlinear relationship between the required displacement of the test mark and that of the optics assembly associated with the test mark when focusing this test mark. This nonlinear relationship can be realized by means of mechanically coupling the displacements using cams or lever mechanisms.

Fundus cameras with automatic focusing adjustment are described in DE 30 31 822 C2 and DE 31 16 380 C2. At least one focusing mark is projected by an optical projection device on the fundus of a human eye to be examined. A detector unit determines the position of the focusing mark. When evaluating the output signal of the detector, an automatic focusing of the fundus camera is carried out by a control unit in that motor-actuated optical elements for imaging the focusing mark are displaced along the optical axis. However, it is also possible to displace the optical elements manually. The solution disclosed in DE 30 31 822 C2 provides, for example, a three-armed connecting lever which is swivelable around its bearing axis. The first lever arm communicates with a focusing lens and the second lever arm communicates with a focusing mark projection device to displace them in direction of the optical axis. The remaining, third lever arm is coupled with an actuating shaft by a pin/slot connection so that when the actuating shaft is swiveled the two other lever arms carry out the corresponding movements along the optical axis.

The disadvantage in this mechanical coupling consists in that the required synchronization between the focusing lens and a focusing mark projection device can be achieved only in a certain focusing range. It is difficult, if not impossible, to compensate for tolerances in the optics assemblies, for example.

U.S. Pat. No. 4,196,979 describes a device for adjusting the distance between an eye and an eye examination device, particularly for examining or photographing the fundus. The described device further contains an arrangement for focusing the image on the fundus. This arrangement likewise comprises an imaging lens and an optical unit for projecting a focusing mark which are mechanically coupled and can be displaced in direction of the optical axis. Here again, the required synchronous running of the assemblies can be realized only with difficulty because of their nonlinear movement. Accordingly, compensating for tolerances in the optics assemblies is difficult, if not impossible.

OBJECT AND SUMMARY OF THE INVENTION

It is the primary object of the present invention to improve the known technical solutions in such a way that the necessary synchronization between the focusing lens and focusing mark projection unit is ensured over a large focusing range in a simple manner and tolerances of the optics assemblies can be compensated.

According to the invention, this object is met by a focusing device for opthalmological equipment based on the nonmydriatic principle, in particular fundus cameras, comprising a projection unit which projects at least one focusing mark in the infrared spectral region on a surface in the eye and a focusing unit. The projection unit and focusing unit are displaceable along the optical axis. The projection unit is arranged in an illumination beam path and the focusing unit is arranged in an observation beam path. A control unit is provided. Displacement of the projection unit and focusing unit is carried out simultaneously or individually by electronically controllable adjusting elements based on corresponding presets of the control unit.

The object is also achieved, in accordance with the invention, by a focusing method for opthalmological equipment based on the nonmydriatic principle, in particular fundus cameras, comprising the following steps: projecting at least one focusing mark in the infrared spectral region on a surface in the eye from a projection unit; providing a focusing unit; providing that the projection unit and focusing unit are displaceable along the optical axis; arranging the projection unit in an illumination beam path; arranging the focusing unit in an observation beam path; providing a control unit; and providing that the projection unit and the focusing unit can be displaced simultaneously or individually by electronically controllable adjusting elements based on the corresponding presets of the control unit.

In the present solution for opthalmological equipment using the nonmydriatic principle, in particular fundus cameras, the device comprises a projection unit which projects at least one focusing mark in the infrared spectral region on a surface in the eye and a focusing unit, both of which are displaceable along the optical axis. According to the method, the projection unit which is arranged in an illumination beam path and the focusing unit which is arranged in an observation beam path are displaced simultaneously or individually by electronically controllable adjusting elements based on the corresponding presets of a control unit that is provided.

The suggested technical solution is usable for opthalmological equipment in which test marks of focusing means are projected over an illumination beam path and are imaged over an observation beam path and in which different optical elements are used in the two beam paths.

The invention is described in more detail in the following with reference to embodiment examples.

DESCRIPTION OF THE PREFERRED EMBODIMENTS

The focusing device according to the invention for opthalmological equipment based on the nonmydriatic principle, in particular fundus cameras, comprises a projection unit which projects at least one focusing mark in the infrared spectral region on a surface in the eye and a focusing unit, both of which are displaceable along the optical axis. The projection unit is arranged in an illumination beam path and the focusing unit is arranged in an observation beam path. The projection unit and the focusing unit can be displaced simultaneously or individually by electronically controllable adjusting elements according to the corresponding presets in an existing control unit having a memory.

Actuating motors, preferably stepper motors, are used as electronically controllable adjusting elements.

The focusing device can further have an autofocusing system for focusing the focusing mark in the infrared spectral region.

Figure 1:
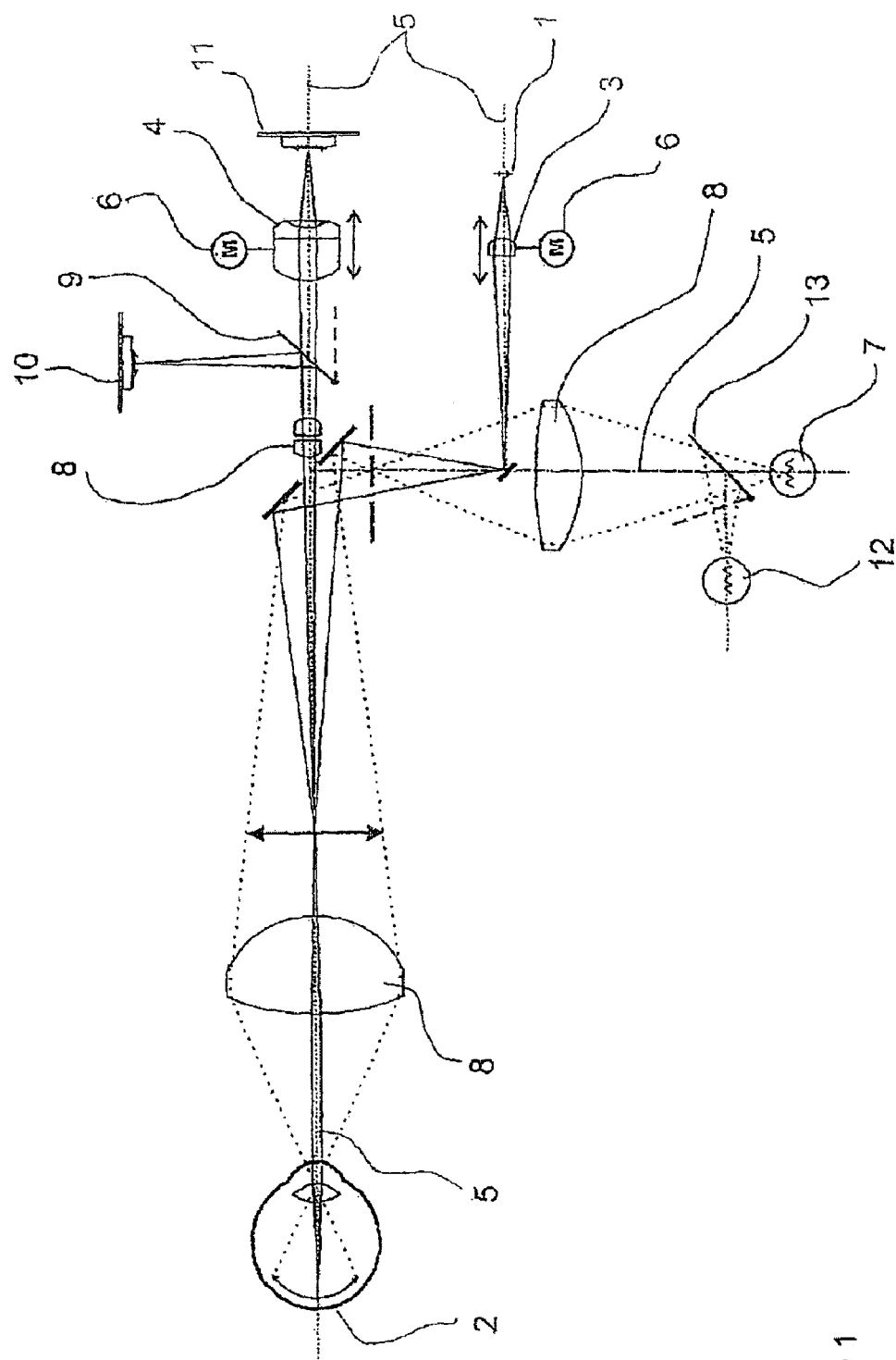
FIG. 1 shows the basic construction of a fundus camera with focusing unit and focusing mark projection unit.

FIG. 1 shows the basic construction of a fundus camera with the focusing device. The focusing device for a fundus camera according to the nonmydriatic principle comprises a projection unit 3 which projects a focusing mark 1 in the infrared spectral region on the fundus 2 and a focusing unit 4, both of which are displaceable along the optical axis 5. The displacement of the projection unit 3 and focusing unit 4, which is preferably realized by means of stepper motors 6, can be carried out simultaneously or individually according to the corresponding presets of a supplied control unit (not shown).

The fundus 2 is illuminated by infrared light coming from an illumination source 7 for observing by means of different optical elements 8. The infrared light reflected by the fundus 2 is imaged on the range finder camera 10 by different optical elements 8 and a fold-out mirror 9.

The fundus 2 is illuminated briefly with white light coming from a strobe source 12 for image recording by a fold-out mirror 13 and different optical elements 8. The white light reflected by the fundus 2 is imaged on the documentation camera 11 by different optical elements 8 with the fold-out mirror 9 in the folded-out state.

Due to optical factors, the focal planes are different for different wavelengths of the illumination light. To compensate for these different focal planes and for possible defective vision of the patent, the fundus camera must be focused. In order to ensure the necessary synchronizing of the projection unit 3 and the focusing unit 4, both units are adjusted by a stepper motor 6. The necessary relationship between the adjusting paths and steps is stored in the control unit as a table or function.

Figure 2:
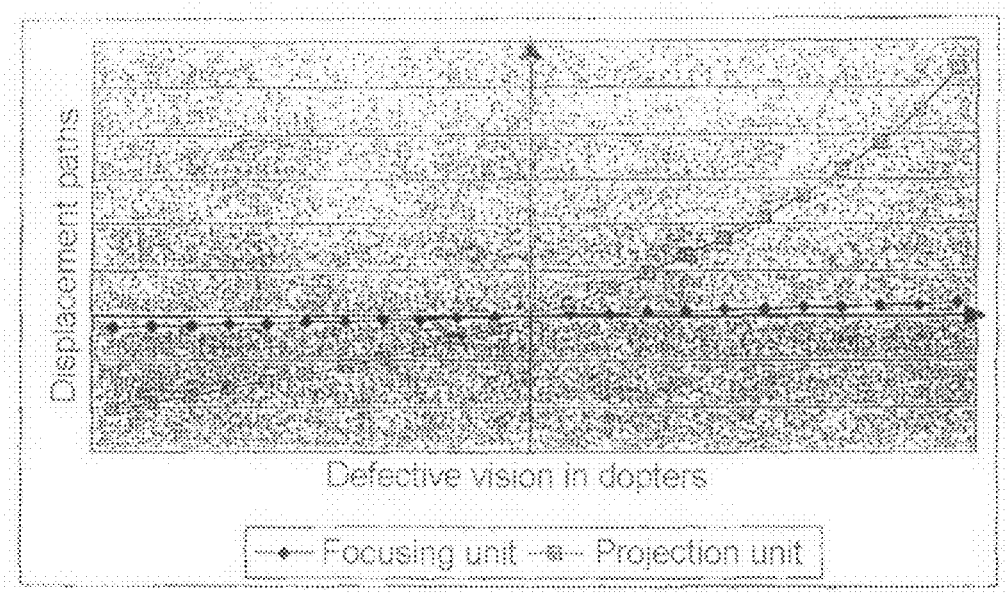
FIG. 2 shows a possible relationship between the movement paths of movements of the focusing unit and focusing mark projection unit.

FIG. 2 shows a possible relationship for the movement paths of the projection unit 3 and focusing unit 4 in a fundus camera according to FIG. 1.

While the movement path for the focusing unit 4 proceeds almost linear to the dioptric values (defective vision) of the patient, the movement path for the projection unit 3 deviates sharply from a linear path. This results in adjustments paths of approximately +/−2 mm for the focusing unit 4 and approximately +/−15 mm for the projection unit 3 of the fundus camera described above. The intersection of the two movement paths is situated at 0 diopters.

In the focusing method, according to the invention, for opthalmological equipment based on the nonmydriatic principle, in particular fundus cameras, at least one focusing mark in the infrared region is projected on a surface in the eye by a projection unit arranged in an illumination beam path and is imaged on a detector by a focusing unit arranged in the observation beam path.

The focusing process is carried out by simultaneous displacement of the projection unit and focusing unit in direction of the optical axis by means of electronically controllable adjusting elements according to the corresponding presets of a control unit. Owing to the fact that different optical elements are used in the illumination beam path and observation beam path, there is a complicated nonlinear relationship between the required displacement of the projection unit and focusing unit.

Therefore, the simultaneous displacement of the projection unit and focusing unit is carried out by means of electronically controllable adjusting elements according to the corresponding presets of the control unit. A corresponding table or function, for example, is stored in the memory of the control unit.

The simultaneous displacement of the projection unit and focusing unit by means of the electronically controllable adjusting elements according to the corresponding presets of the control unit can also be carried out automatically by an autofocusing system after the opthalmological equipment has been directed toward the patient.

After the focusing mark in the infrared spectral region has been focused by the simultaneous displacement of the projection unit and focusing unit, only the focusing unit is displaced along the optical axis when changing to the image recording mode (visible spectral region). The electronically controllable adjusting element is controlled by the control unit according to the presets in memory and the displacement is then canceled after the image is recorded.

Owing to the spectral characteristic of the fundus, the focusing mark projected in the infrared spectral region on the fundus is reflected in a deeper layer of tissue than the white light used for image recording. While white light is reflected by the retina, infrared light penetrates through the retina and is first reflected by the pigmentary epithelium lying below the retina. Accordingly, the focal planes of white light and infrared light are separated by a distance of about 200 µm which corresponds to the known average thickness of the retina. When changing to the image recording mode, this is corrected by displacing the focusing unit by the corresponding value. In the present example, the focusing unit is displaced by steps of approximately 50 µm.

The displacements carried out by the electronically controllable adjusting elements are preferably effected in defined steps.

The corresponding default values stored in the memory of the control unit for the displacement of the projection unit and focusing unit, or of the focusing unit only, are preset or are recorded and stored by means of reference objects.

The series of movements can be recorded, for example, point by point. For this purpose, the focusing mark of the projection unit is projected on a receiving plane, the sharp focusing of the focusing mark being monitored by the rangefinder camera, and the setting of the stepper motor at which a sharp focus is achieved is stored. The focusing mark which is sharply imaged on the receiving plane is imaged on the documentation camera by the focusing unit and the setting of the stepper motor at which a sharp imaging is achieved is stored. This process is repeated as often as necessary for different dioptric values. After a finite number of reference points (value pairs) have been recorded, the remaining value pairs are determined by a compensating curve.

This point-by-point recording of the movement paths has the advantage that device-specific tolerances of the optics assemblies in particular can be taken into account and the movement paths are accurately matched to the device.

The necessary synchronous running between the projection unit and a focusing unit can be ensured in a simple manner by means of the inventive solution. Accordingly, not only can the sequence of displacement paths be optimally adapted over the entire focusing range, but the tolerances of the optics assemblies can also be compensated in a simple manner from one device to another.

Necessary changes in the focal plane which are needed when switching between observation mode (in the infrared spectral region) and image recording mode (in the visible spectral region) can be implemented in a simple manner by displacing the focusing unit when changing over. After the images are recorded, the focusing state prior to the image recording is restored by the control unit. The displacing paths required for switching between modes can also be stored in tabular form.

By means of the solution described above, adapting between a projection unit and a focusing unit can be carried out with greater accuracy than was possible with a purely mechanical coupling and the solution is appreciably more flexible. Switching the focal plane between the infrared spectral region and visible spectral region can likewise be realized with the same arrangement without having to introduce and remove additional optical assemblies.

While the foregoing description and drawings represent the present invention, it will be obvious to those skilled in the art that various changes may be made therein without departing from the true spirit and scope of the present invention.

What is claimed is:

1. A focusing device for opthalmological equipment based on the nonmydriatic principle, in particular fundus cameras, comprising:
   a projection unit which projects at least one focusing mark in the infrared spectral region on a surface in the eye;
   a focusing unit;
   said projection unit and focusing unit being displaceable along the optical axis;
   said projection unit being arranged in an illumination portion of an illumination beam path and said focusing unit being arranged in an observation beam path, where the illumination portion of the illumination beam path, in which the projection unit is arranged, is separate and distinct from the observation beam path; and
   a control unit;
   wherein said displacement of the projection unit and focusing unit can be carried out both simultaneously and individually, or in the alternative, by electronically controllable adjusting elements based on corresponding presets of said control unit.

2. The focusing device according to claim 1;
   wherein actuating motors, such as stepper motors, are used as electronically controllable adjusting elements.

3. The focusing device according to claim 1;
   wherein the control unit has a memory.

4. The focusing device according to claim 1;
   wherein an autofocusing system is provided for focusing the focusing mark in the infrared spectral region.

5. The focusing device according to claim 1;
   wherein the corresponding presets of said control unit included the different adjusting paths of the projection unit and focusing unit.

6. The focusing device according to claim 1;
   wherein the corresponding presets of the control unit are complicated nonlinear relationships between the required displacement of the projection unit and focusing unit.

7. The focusing device according to claim 1;
   wherein the corresponding presets stored in the control unit as a table or function.

8. A focusing method for opthalmological equipment based on the nonmydriatic principle, in particular fundus cameras, comprising the following steps:
   providing a projection unit which projects at least one focusing mark in the infrared spectral region on a surface in the eye;
   providing a focusing unit;
   providing that said projection unit and focusing unit are displaceable along the optical axis;
   arranging said projection unit in an illumination portion of an illumination beam path;
   arranging said focusing unit in an observation beam path;
   providing that the illumination portion of the illumination beam path, in which the projection unit is arranged, is separate and distinct from the observation beam path; and
   providing a control unit;

wherein said displacement of the projection unit and focusing unit can be carried out both simultaneously and individually, or in the alternative, by electronically controllable adjusting elements based on corresponding presets of the control unit.

9. The focusing method according to claim 8;
wherein the opthalmological equipment is directed toward the patient and the focusing is carried out by simultaneous displacement of the projection unit and focusing unit by the electronically controllable adjusting elements based on the corresponding presets of the control unit.

10. The focusing method according to claim 9;
wherein the focusing is carried out by simultaneous displacement of the projection unit and focusing unit by the electronically controllable adjusting elements based on the corresponding presets of a control unit automatically by an autofocusing system after the opthalmological equipment has been directed toward the patient.

11. The focusing method according to claim 8;
wherein, in order to change to the image recording mode after focusing by the simultaneous or individual displacement of the projection unit and focusing unit, at least the focusing unit is displaced by the electronically controllable adjusting element according to the presets of the control unit.

12. The focusing method according to claim 8;
wherein the displacements carried out by the electronically controllable adjusting elements are preferably carried out in defined steps.

13. The focusing method according to claim 8;
wherein the corresponding default values stored in the memory of the control unit for the displacement of the projection unit and focusing unit, or of the focusing unit only, are preset or are recorded by reference objects.

* * * * *